(12) United States Patent
Wei et al.

(10) Patent No.: US 7,679,758 B2
(45) Date of Patent: Mar. 16, 2010

(54) FASTENER INSPECTION SYSTEM AND METHOD

(75) Inventors: Wong Su Wei, Singapore (SG); Victor Vertoprakhov, NovosiBirsk (RU); Zhou Wensen, Singapore (SG); Noor Ashedah Binti Jusoh, Singapore (SG); Tian Poh Yew, Singapore (SG); Ah Kow Chin, Johor (MY); Chee Leong Chua, Singapore (SG)

(73) Assignee: Microview Technologies PTE Ltd., Singapore (SG)

( * ) Notice: Subject to any disclaimer, the term of this patent is extended or adjusted under 35 U.S.C. 154(b) by 1330 days.

(21) Appl. No.: 11/118,649

(22) Filed: Apr. 29, 2005

(65) Prior Publication Data

US 2006/0244953 A1 Nov. 2, 2006

(51) Int. Cl.
| G01B 11/14 | (2006.01) |
| G01N 21/00 | (2006.01) |
| H04N 9/47 | (2006.01) |
| H04N 7/18 | (2006.01) |
| G06K 9/00 | (2006.01) |
| B07C 5/00 | (2006.01) |

(52) U.S. Cl. ............ 356/625; 356/237.1; 348/86; 348/91; 348/125; 382/141; 382/152; 209/576; 209/586; 209/929

(58) Field of Classification Search ............... None
See application file for complete search history.

(56) References Cited

U.S. PATENT DOCUMENTS

| 4,828,100 | A | * | 5/1989 | Hoppmann et al. | ......... 198/392 |
| 5,661,249 | A | * | 8/1997 | Rupp et al. | ................ 73/865.8 |
| 5,823,356 | A | * | 10/1998 | Goodrich et al. | ............ 209/601 |
| 6,578,699 | B2 | * | 6/2003 | Baird et al. | ................ 198/392 |
| 7,364,043 | B2 | * | 4/2008 | Ong et al. | ................... 209/652 |

* cited by examiner

*Primary Examiner*—Tarifur Chowdhury
*Assistant Examiner*—Gordon J Stock, Jr.
(74) *Attorney, Agent, or Firm*—Jackson Walker L.L.P.; Christopher J. Rourk (57) ABSTRACT

A method of optically inspecting a fastener to determine whether it meets two or more dimensional parameters is provided. The method includes using centrifugal force to place the fastener in a predetermined location. Two or more sets of image data of the fastener are generated from two or more corresponding different angles. Fastener pass/fail data is generated using a dimensional requirement associated with each set of image data.

20 Claims, 5 Drawing Sheets

FASTENER INSPECTION SYSTEM AND METHOD

FIELD OF THE INVENTION

The invention relates to optical inspection of objects to determine whether they meet required manufacturing specifications, and in particular to the optical inspection of fasteners.

BACKGROUND OF THE INVENTION

It is known to optically inspect manufactured items for defects that would render the item unusable, such as by combining a fastener inspection system with a single camera. The inspection of fasteners may include examining threaded fasteners to ensure that the threaded portion is correctly formed, that the fastener head is correctly formed, that the junction of the head and shank is correctly formed, that the shank is correctly formed at the terminal end, and other suitable examinations.

One drawback to prior methods and systems is that the optical inspection software must be able to match the object against a library of acceptable objects regardless of its orientation and lighting, and this must be done in a rapid manner. While some of these problems can be solved by initially orienting the object in only one position and then moving it to other pre-determined positions, the recognition software must still track the object and recognise it once it has reached the new orientation. This process requires a computationally intensive operation that can be the limiting factor in the production and quality control of the fasteners.

SUMMARY OF THE INVENTION

In accordance with the present invention, a system and method for inspecting fasteners are provided that overcome known problems with systems and methods for inspecting fasteners.

In particular, a system and method for inspecting fasteners are provided which utilize dual inspection angles and on-the-fly selection of comparison images to provide additional inspection capabilities and flexibility.

In accordance with an exemplary embodiment of the present invention, a method of optically inspecting a fastener to determine whether it meets two or more dimensional parameters is provided. The method includes using centrifugal force to place the fastener in a predetermined location. Two or more sets of image data of the fastener are generated from two or more corresponding different angles. Fastener pass/fail data is generated using a dimensional requirement associated with each set of image data.

The present invention provides many important technical advantages. One important technical advantage of the present invention is a fastener inspection system that utilizes images of the fasteners from two different axes and that selects comparison image data on the fly, so as to provide additional inspection capabilities and flexibility.

Those skilled in the art will further appreciate the advantages and superior features of the invention together with other important aspects thereof on reading the detailed description that follows in conjunction with the drawings.

DETAILED DESCRIPTION OF PREFERRED EMBODIMENTS

In the description that follows, like parts are marked throughout the specification and drawings with the same reference numerals, respectively. The drawing figures might not be to scale, and certain components can be shown in generalized or schematic form and identified by commercial designations in the interest of clarity and conciseness.

Figure 1:
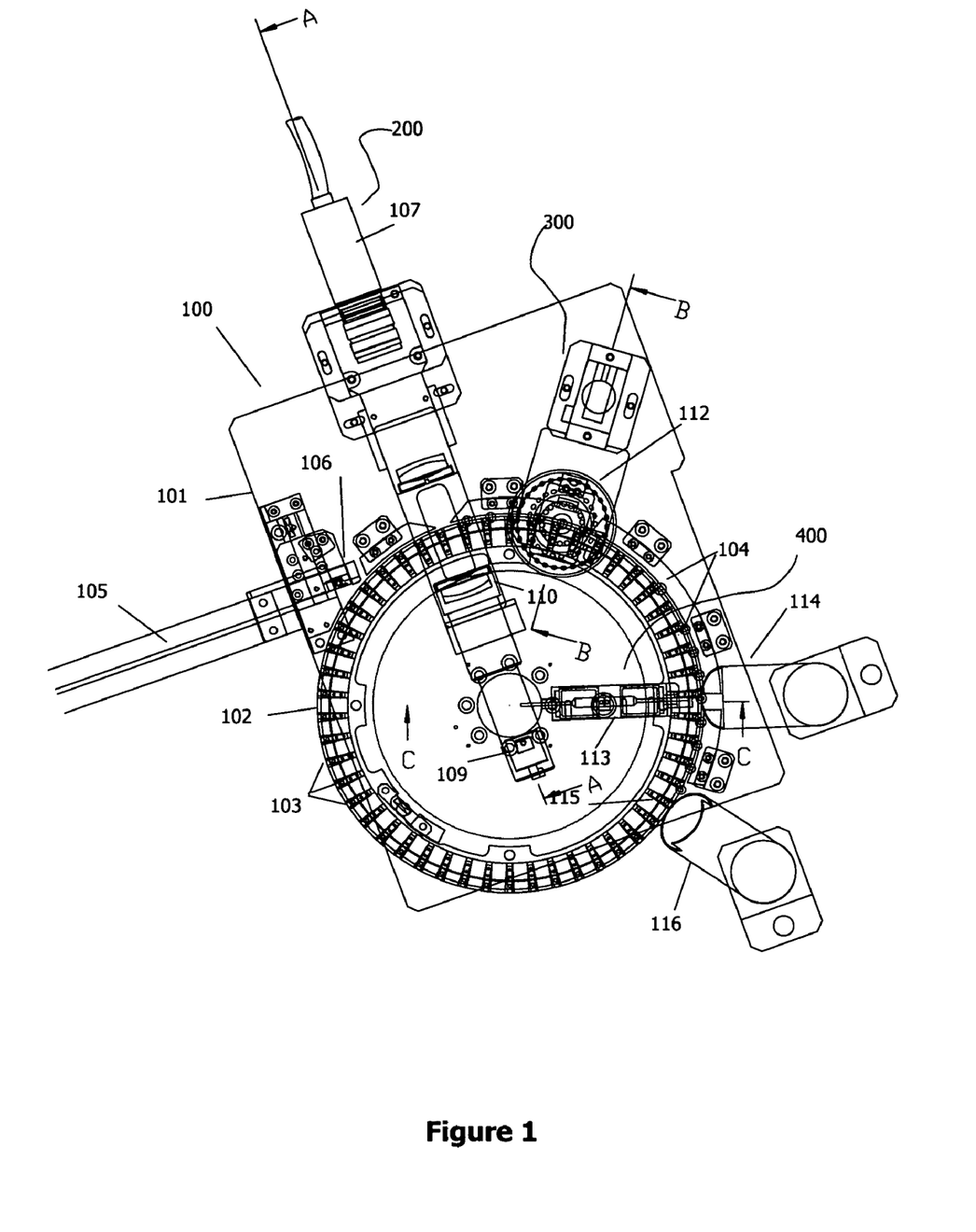
FIG. 1 is a diagram an inspection station in accordance with an exemplary embodiment of the present invention.

FIG. 1 is a diagram an inspection station 100 in accordance with an exemplary embodiment of the present invention. Inspection station 100 allows the top dimension of fasteners to be inspected, with compensation for variations in surface finish.

Inspection station 100 includes base 101 having on it a rotating turntable 102. Singulating feed mechanism 106 provides fasteners 104 to rotating turntable 102, and the fasteners 104 are fed into fastener retaining slots 103 by centrifugal force, where they can be inspected by inspection system 700 (not explicitly shown) using image data generated by horizontal vision system 200, vertical vision system 300, and other suitable systems. Inspection system 700 generates rejection data, which causes rejection mechanism 400 to actuate and to eject fasteners 104 that do not meet inspection criteria. If rejection data is not generated, the fasteners 104 are accepted at an acceptance position that includes stationary wiper 115, which removes the acceptable fasteners 104 that remain after the rejected fasteners 104 have been removed.

Rotating turntable 102 has fastener retaining slots 103 around the periphery. Fasteners 104 are fed into the fastener retaining slots 103 from feed chute 105 by singulating feed mechanism 106, which biases a fastener 104 against the turntable so that it locates in one of fastener retaining slots 103. Rotating turntable 102 rotates continuously as fasteners 104 feed into it. View AA of FIG. 1 is shown in greater detail in FIG. 2. VIEW BB of FIG. 1 is shown in greater detail in FIG. 3. View CC of FIG. 1 is shown in greater detail in FIG. 4.

Figure 2:
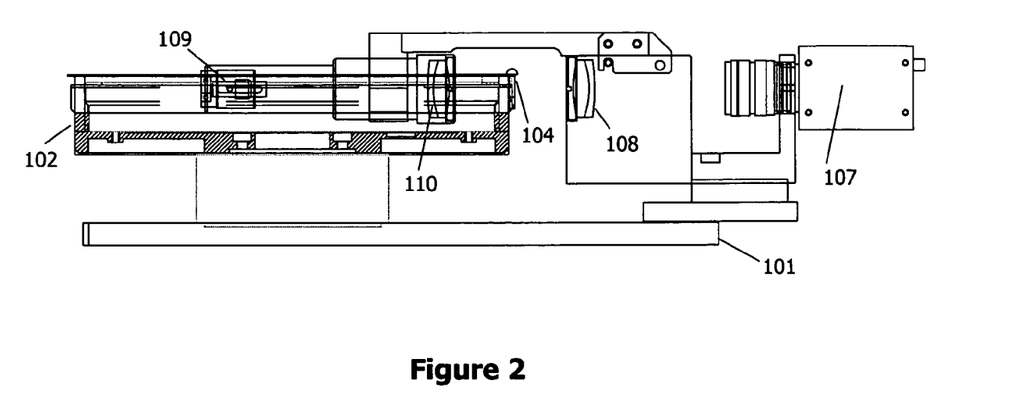
FIG. 2 is a diagram of an inspection station showing a horizontal vision system in accordance with an exemplary embodiment of the present invention.

FIG. 2 is a diagram of inspection station 100 showing horizontal vision system 200 in accordance with an exemplary embodiment of the present invention. After the fasteners 104 are fed onto rotating turntable 102, it turns to present the fasteners 104 first to horizontal inspection camera 107 of the horizontal vision system 200, which views the fastener 104 through optics 108, as illuminated by transmitted light from light source 109 and collimator 110. In this manner, silhouette or shadowgraph data can be generated, the data can be compared against a library of acceptable parameters both to categorize the fastener 104, for the presence of a screw thread of the correct type and pitch, and for the correct dimensions for the fastener type. The light source 109 can have adjustable luminance, and can be adjusted to provide an optimum level of illumination where the contrast of the lighting is approximately the same as the maximum grey scale range of horizontal inspection camera 107.

It is not necessary that rotating turntable 102 remain stationary while the fastener 104 is imaged and categorized since capture of the image can be near instantaneous and once the image is captured the categorization and labeling for rejection will occur while the rotating turntable 102 is indexing onwards.

Figure 3:
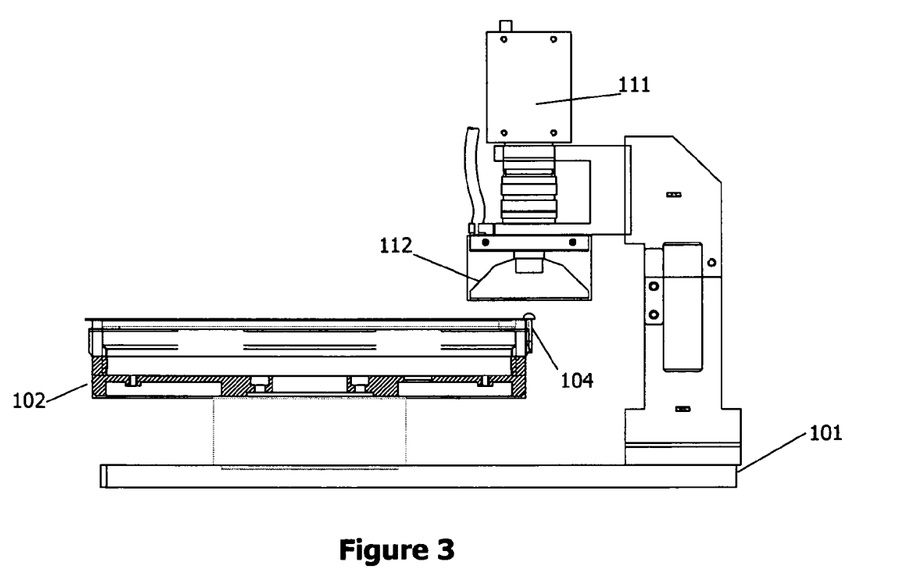
FIG. 3 is a diagram of an inspection station showing a vertical vision system in accordance with an exemplary embodiment of the present invention.

FIG. 3 is a diagram of inspection station 100 showing vertical vision system 300 in accordance with an exemplary embodiment of the present invention. Further rotation of rotating turntable 102 presents the fastener 104 to vertical vision system camera 111, which can include adjustable lighting head 112 to illuminate fastener 104 using reflected light. Adjustable lighting head 112 provides illumination from a range of directions at variable levels in each direction, so as to illuminate each fastener 104 to provide optimum contrast regardless of the finish on the fastener head. In this manner, vertical vision system camera 111 can be used to determine the delineation of depressions on the fastener head, the outline of the exterior of the head, or other fastener dimensions that may be required to allow the fastener to fit a fastener driving tool. Detection of the optimum contrast is by detection of the best differentiation of edges in the viewed image, and requires a pre-programmed illumination routine to vary the illumination from adjustable lighting head 112 so as to narrow the range of choices of illumination.

In one exemplary embodiment, the luminance of adjustable lighting head 112 can be varied rapidly by inspection system 700 or other suitable systems until a level of illumination that provides the greatest contrast is achieved in image data corresponding to the edges found in the fastener 104. The fastener 104, which was initially inspected at the horizontal vision system, can now be further inspected as necessary in terms of external drive profile, internal drive profile, overall diameter, or other suitable data. In another exemplary embodiment, rejection data can be associated with the fastener 104 by inspection system 700 or other suitable systems if the dimensions of the fastener 104 fail to fall within a valid category, for instance because the internal drive socket does not meet specifications.

Figure 4:
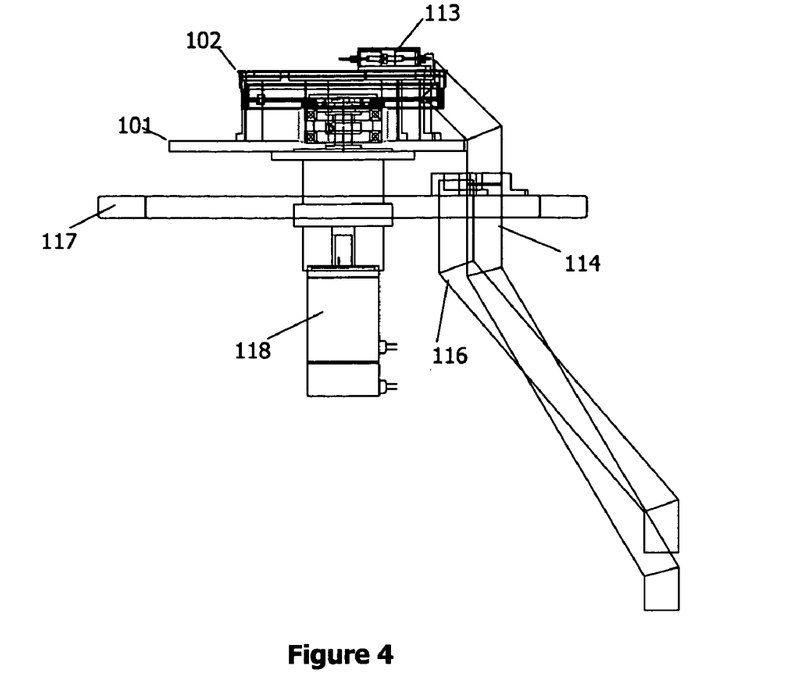
FIG. 4 is a diagram of an inspection station showing a rejection mechanism in accordance with an exemplary embodiment of the present invention.

FIG. 4 is a diagram of inspection station 100 showing rejection mechanism 400, in accordance with an exemplary embodiment of the present invention. Motor 118 can be a servomotor, a stepping motor, or other suitable motors. Rotating turntable 102 is turned by motor 118 and is mounted on base 101. Motor 118 allows the position of the fastener retaining slots 103 as shown in FIG. 1 to be tracked with accuracy so that the fastener retaining slots 103 can be indexed.

As rotating turntable 102 progresses, a fastener 104 that has been determined to be faulty rotates to a position opposite reject solenoid 113, which is controlled so as to operate and eject the fastener 104 down reject chute 114. The remaining fasteners 104 are directed by stationary wiper 115 as shown in FIG. 1 to accept chute 116. Likewise, other suitable processes can be used, such as the use of an accept solenoid in conjunction with controls over singulating feed mechanism 106 of FIG. 1 to allow a fastener 104 to be inspected multiple times, such as when image data of the fastener was not adequately obtained and where additional inspection time is required.

While one accept chute 116 is shown (and can be disposed within element 117, as shown), two or more accept chutes 116 can be used, where suitable. Inspection station 100 can thus act as a sorter using mechanisms similar to the reject mechanism 400, as inspection station 100 can be used to classify the fasteners 104 it inspects as opposed to only determining pass/fail criteria. In one exemplary embodiment, reject mechanism 400 can include a solenoid 113.

Figure 5:
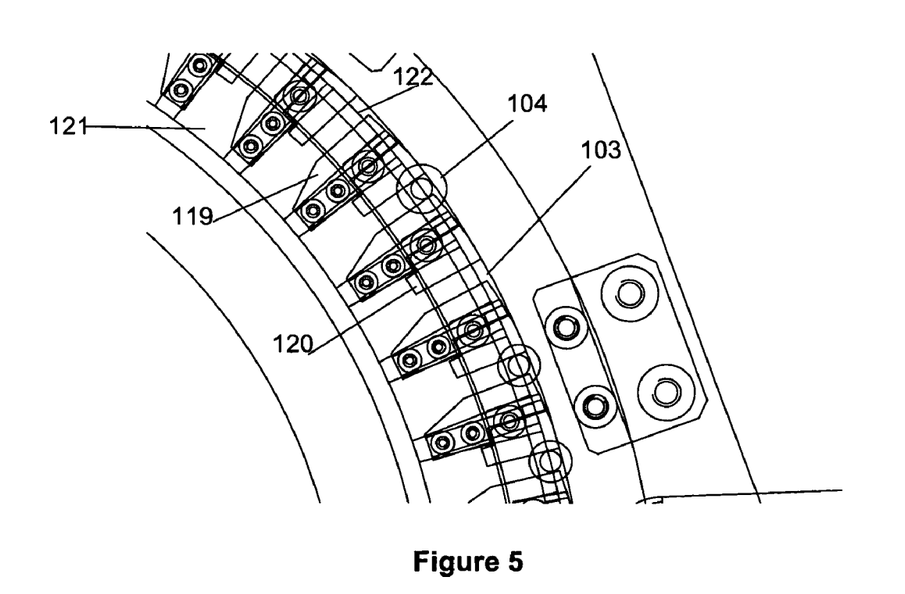
FIG. 5 is an overhead view of the fastener locating mechanism on the rotating turntable in accordance with an exemplary embodiment of the present invention.

FIG. 5 is an overhead view of the fastener locating mechanism on the rotating turntable 102 in accordance with an exemplary embodiment of the present invention. Fasteners 104 are located in fastener retaining slots 103, which are formed by locating fingers 120 of outer turntable ring 122 and locating fingers 119 of inner turntable ring 121. Locating fingers 119 of inner turntable ring 121 are configured so as to guide the fasteners 104 into fastener retaining slots 103. In one exemplary embodiment, inner turntable ring 121 and outer turntable ring 122 can be controllably adjusted so as to increase or decrease the size of fastener retaining slots 103.

Figure 6:
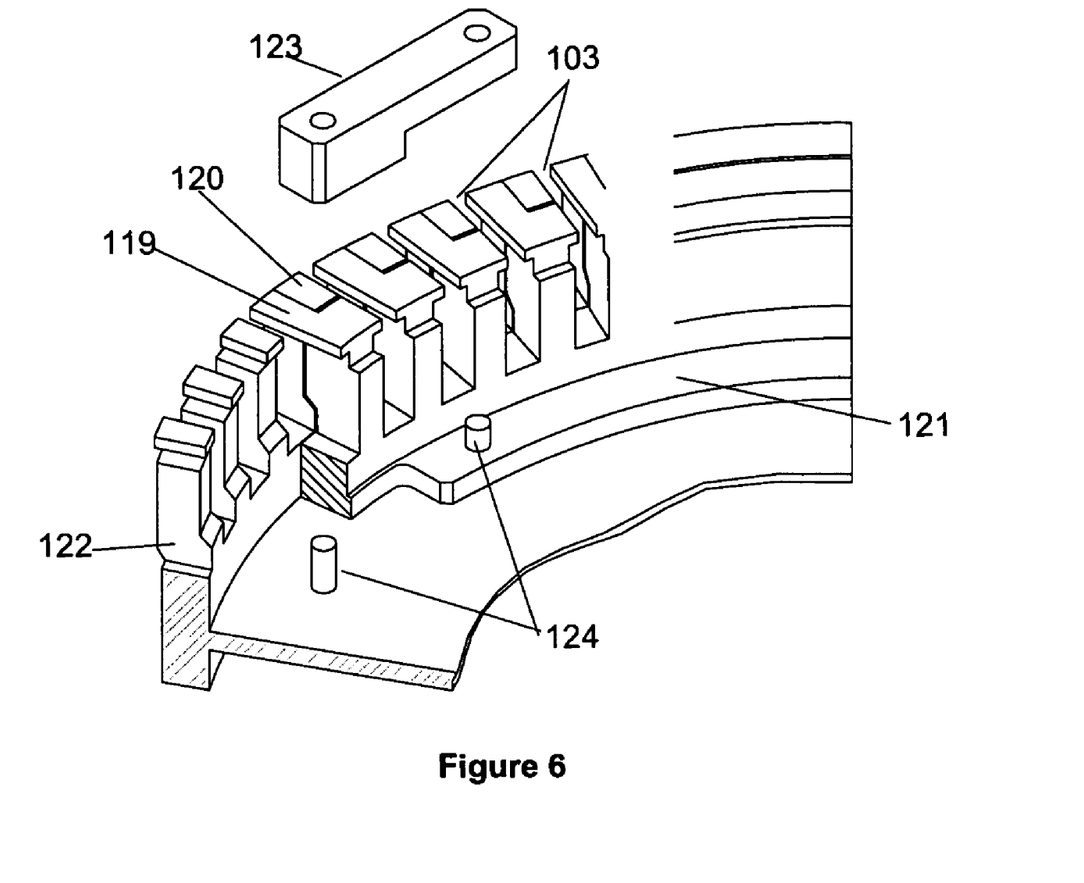
FIG. 6 is a breakaway view of the fastener locating mechanism on the rotating turntable in accordance with an exemplary embodiment of the present invention.

FIG. 6 is a breakaway view of the fastener locating mechanism on rotating turntable 102 in accordance with an exemplary embodiment of the present invention. The fastener locating mechanism on rotating turntable 102 can include an outer turntable ring 122 and an inner turntable ring 121. The outer turntable ring 122 has locating fingers 120, while the inner turntable ring 121 has locating fingers 119. Rotation of the inner turntable ring 121 relative to the outer turntable ring 122 allows control of fastener retaining slots 103 within which the fasteners 104 are located. Rotating turntable 102 can thus be adjusted for fasteners 104 of differing diameter.

Block 123 locates on dowels 124 on the inner turntable ring 121 and outer turntable ring 122 to positively locate the rings relative to each other. Replacement of block 123 with another of different length allows quick changing of the dimensions of fastener retaining slots 103. In one exemplary embodiment, a conical block 123 with increasing diameter or other suitable mechanisms can be used to allow the dimension of fastener retaining slots 103 to be altered on-the-fly.

In one exemplary embodiment, there may be other vision systems present to inspect the thread form in side view by reflected light to determine if the thread is intact. For example, one can be used around the whole fastener 104, and another can be used to inspect the lower tip of a fastener 104. In this exemplary embodiment, the presence of a chisel point in self-drilling fasteners 104 can be detected.

The present invention can be used in conjunction with the inspection of any suitable item that has a substantially regular form in two axes, and can be adapted to the inspection of objects of irregular form with limited re-entrant portions. Use in this latter application requires orienting the object on two axes for inspection, rather than the single axis orientation described for the current invention. Such orientation techniques are known. Use of both reflected light and transmitted light to provide sufficient detail of a single axis can also or alternatively be used.

In addition to a rotating turntable 102, other suitable conveying systems can also or alternatively be used, such as ones that are capable of orienting and retaining the object to be recognized.

It is to be understood that even though numerous characteristics and advantages of the various embodiments of the present invention have been set forth in the foregoing description, together with details of the structure and functioning of various embodiments of the invention, this disclosure is illustrative only, and changes may be made in detail so long as the functioning of the invention is not adversely affected. For example the particular elements of the conveyor or rotating turntable 102 may vary dependent on the particular application for which it is used without variation in the spirit and scope of the present invention.

Figure 7:
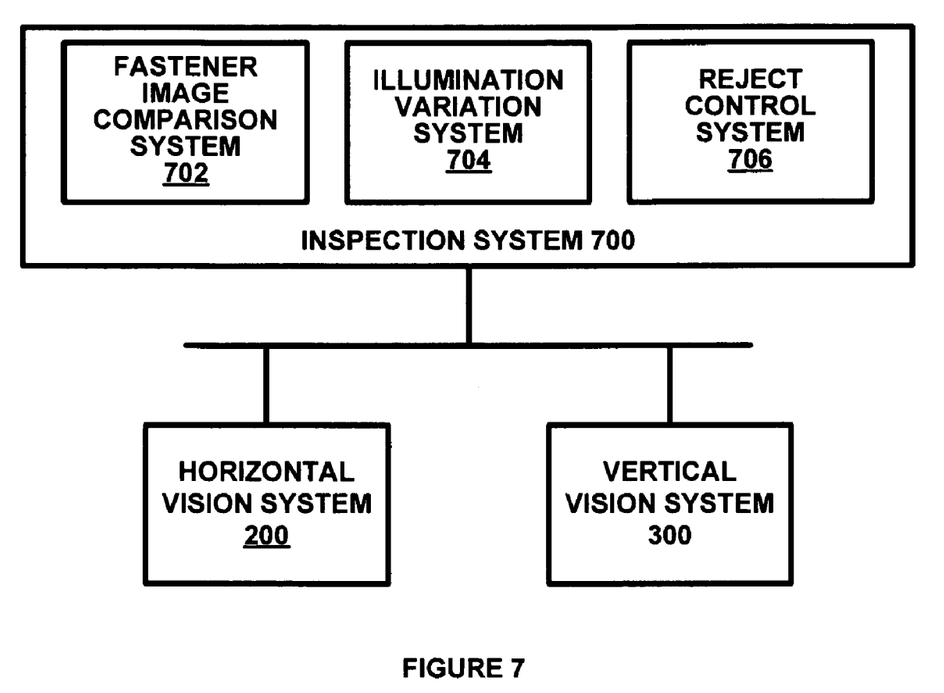
FIG. 7 is a diagram of an inspection system in accordance with an exemplary embodiment of the present invention.

FIG. 7 is a diagram of inspection system 700, in accordance with an exemplary embodiment of the present invention. Inspection system 700 can be implemented in hardware, software, or a suitable combination of hardware and software, and can be one or more software systems operating on a general-purpose processing platform. Inspection system 700 is coupled to horizontal vision system 200 and vertical vision system 300 and can use suitable image processing techniques to inspect image data of the fasteners 104 that is generated by horizontal vision system 200 and vertical vision system 300.

As used herein, a software system can include one or more objects, agents, threads, lines of code, subroutines, separate software applications, two or more lines of code or other suitable software structures operating in two or more software applications or on two or more processors, or other suitable software structures. In one exemplary embodiment, a software system can include one or more lines of code or other suitable software structures operating in a general purpose software application, such as an operating system, and one or more lines of code or other suitable software structures operating in a specific purpose software application.

Inspection system 700 includes fastener image processing system 702, illumination variation system 704, and reject control system 706. In one exemplary embodiment, fastener image processing system 702 includes a library of expected fastener parameters with associated tolerances for the length, diameter, head profile, presence of washer, profile of fastener tip, thread profile and pitch, and other suitable data. Fastener image processing system 702 allows rapid categorization of the currently illuminated fastener 104 and analysis of the dimensional data of the currently illuminated fastener 104, based on tolerance data. If fastener image processing system 702 determines that the currently illuminated fastener 104 does not meet predetermined tolerance criteria, it generates fastener rejection data. In addition, fastener image processing system 702 can generate illumination variation data if the image data of the currently illuminated fastener does not generate predetermined match data, such as if a match is not found, if one or more critical dimensions can not be determined, or in response to other suitable conditions.

Illumination variation system 704 receives illumination variation data and generates control data of one or more lighting devices to controllably vary the luminance generated by the lighting devices. In one exemplary embodiment, illumination variation system 704 can use one or more predetermined settings or functions to vary the luminance of the lighting devices, such as to continuously increase or decrease the luminance, increase or decrease the luminance by a predetermined step, or other suitable settings or functions.

Reject control system 706 receives fastener rejection data and generates fastener rejection control data. In one exemplary embodiment, reject control system 706 can receive turntable dimension data, turntable rotation data, inspection position data, reject slot position data, and other suitable data and can generate reject control timing data to allow the rejected fastener 104 to be ejected by a suitable mechanism when it reaches a predetermined position. Likewise, control timing data can be stored, can be associated with an interchangeable turntable, or other suitable processes can be used.

Although exemplary embodiments of a system and method of the present invention have been described in detail herein, those skilled in the art will also recognize that various substitutions and modifications can be made to the systems and methods without departing from the scope and spirit of the appended claims.

What is claimed is:

1. A method of optically inspecting a fastener to determine whether the fastener meets two or more dimensional parameters comprising:
   using centrifugal force to place the fastener in a predetermined location;
   generating two or more sets of image data of the fastener from two or more corresponding different angles;
   generating fastener pass/fail data using a dimensional requirement associated with each set of image data; and
   adjusting a first turntable ring coupled to a plurality of first finger segments relative to a second turntable ring coupled to a plurality of second finger segments to adjust a slot width of a plurality of slots.

2. The method of claim 1 wherein the fastener is separately illuminated for each set of image data.

3. The method of claim 1 wherein illumination for at least one set of image data is varied to provide an optimum contrast of the fastener for generation of the pass/fail data.

4. The method of claim 1 further comprising removing the fastener based on the fastener pass/fail data.

5. The method of claim 1 wherein the fastener is threaded.

6. The method of claim 1 wherein the fastener is viewed by at least one optical system of a vision system in transmitted light and by at least one other optical system of a different vision system in reflected light.

7. The method of claim 6 wherein the fastener is located on a rotating turntable and the vision systems are located with at least one camera above the rotating turntable and one camera beside the rotating turntable.

8. An optical inspection station comprising:
   a conveying system;
   a first optical vision system for generating first image data of an object on the conveying system from a first plane of the object;
   a second optical vision system for generating second image data of the object on the conveying system from a second plane of the object;
   a defective object removal system for receiving defective object removal data generated from the first image data and the second image data and moving the conveying system so as to cause a defective object to be removed from the conveying system;
   a second removal system for removing all remaining objects from the conveying system; and
   wherein the conveying system comprises a rotary platform or turntable having an inner ring having fingers defining one side of each of a plurality of radial slots, an outer ring having fingers defining a second side of each of the plurality of radial slots and wherein a width of each of the plurality of radial slots can be adjusted by varying a relative circumferential position of the rings.

9. The optical inspection station of claim 8 wherein at least one of the optical vision systems operates using reflected light.

10. The optical inspection station of claim 8 wherein the luminance of a light source of at least one optical vision system can be controlled to optimise a perceived contrast.

11. The optical inspection station of claim 8 further comprising multiple object acceptance positions.

12. The optical inspection station of claim 8 wherein the platform or turntable can rotate continuously during inspection.

13. The optical inspection station of claim 8 wherein the object to be inspected is a fastener.

14. The optical inspection station of claim 8 wherein the object can be retained within one of the radial slots in the platform or turntable during inspection.

15. The optical inspection station of claim 13 wherein the fastener has a head and a shank, the head extends above the plane of the conveying system, and the shank extends normal to the plane of the conveying system.

16. The optical inspection station of claim 14 wherein the width of one or more of the radial slots may be adjusted for differing object dimensions.

17. An optical inspection station comprising:
a conveying system;
a first optical vision system for generating first image data of an object on the conveying system from a first plane of the object;
a second optical vision system for generating second image data of the object on the conveying system from a second plane of the object;
a defective object removal system for receiving defective object removal data generated from the first image data and the second image data and moving the conveying system so as to cause a defective object to be removed from the conveying system;
a second removal system for removing all remaining objects from the conveying system; and
wherein the conveying system comprises a rotary platform or turntable having an inner ring having fingers defining one side of each of a plurality of radial slots, an outer ring having fingers defining a second side of each of the plurality of radial slots and wherein a width of each of the plurality of radial slots can be adjusted by varying a relative circumferential position of the rings, wherein at least one of the optical vision systems operates using reflected light and the object to be inspected is a fastener.

18. The optical inspection station of claim 17 wherein the luminance of a light source of at least one optical vision system can be controlled to optimise a perceived contrast.

19. The optical inspection station of claim 17 wherein the fastener has a head and a shank, the head extends above the plane of the conveying system, and the shank extends normal to the plane of the conveying system.

20. The optical inspection station of claim 17 further comprising multiple object acceptance positions.

* * * * *

UNITED STATES PATENT AND TRADEMARK OFFICE
CERTIFICATE OF CORRECTION

| | |
|---|---|
| PATENT NO. | : 7,679,758 B2 |
| APPLICATION NO. | : 11/118649 |
| DATED | : March 16, 2010 |
| INVENTOR(S) | : Wong Soon Wei et al. |

It is certified that error appears in the above-identified patent and that said Letters Patent is hereby corrected as shown below:

Title Page 1, section (75) - Inventors - "Wong Su Wei" should be changed to -- Wong Soon Wei --.

Signed and Sealed this

Fourth Day of May, 2010

David J. Kappos
*Director of the United States Patent and Trademark Office*